United States Patent [19]

Dardik et al.

[11] 3,974,526

[45] Aug. 17, 1976

[54] VASCULAR PROSTHESES AND PROCESS FOR PRODUCING THE SAME

[76] Inventors: Irving I. Dardik, 130 DeVriese Court, Tenafly, N.J. 07670; Herbert Dardik, 806 Washburn St., Teaneck, N.J. 07666

[22] Filed: Jan. 23, 1975

[21] Appl. No.: 543,462

Related U.S. Application Data

[63] Continuation-in-part of Ser. No. 376,948, July 6, 1973, Pat. No. 3,894,530.

[52] U.S. Cl. .................................... 3/1.4; 128/1 R; 128/334 R
[51] Int. Cl.² ...................... A61F 1/24; A61B 19/00
[58] Field of Search.......... 3/1, 1.4; 128/1 R, 334 R, 128/334 C, 335, 335.5

[56] References Cited
UNITED STATES PATENTS

| | | | |
|---|---|---|---|
| 3,425,418 | 2/1969 | Chvapil et al. | 3/1.4 X |
| 3,562,820 | 2/1971 | Braun | 3/1.4 |
| 3,894,530 | 7/1975 | Dardik et al. | 3/1.4 X |

OTHER PUBLICATIONS
"The Use of Umbilical Cord for Reconstruction of Abdominal Wall Defects" by Frederick C. Heaton et al., *Surgical Forum*, vol. 21, 1970, pp. 56–57.

*Primary Examiner*—Ronald L. Frinks
*Attorney, Agent, or Firm*—Blum, Moscovitz, Friedman & Kaplan

[57] ABSTRACT

A process for producing tubular prostheses for use in vascular reconstructive surgery is described. The invention comprises chemically and structurally modifying the veins and arteries of the human umbilical cord to obtain a vascular grafting material which is superior to existing blood vessel substitutes. The process involves the steps of (a) removing the internal veins and arteries of the umbilical cord from its outer tissue; (b) separating these vessels from one another; (c) treating the vessels with cleansing and tanning agents to eliminate antigenicity; (d) shaping the vessels by inserting a mandrel; and (e) applying a mesh support to the shaped and tanned prosthesis. The process of repairing, replacing and augmenting a human and animal vein or artery using the prosthesis produced by the process is also described.

39 Claims, No Drawings

VASCULAR PROSTHESES AND PROCESS FOR PRODUCING THE SAME

This is a continuation-in-part of the applicant's co-pending application Ser. No. 376,948, filed July 6, 1973, now U.S. Pat. No. 3,894,530.

BACKGROUND OF THE INVENTION

The search for the ideal blood vessel substitute has to date focused on biologic tissues and synthetics. Variations upon simple substitution with these materials have included such innovations as heparin bonding, endothelial coating with cells grown in tissue culture, and in vivo collagen tube formation on silicone mandrels. Despite intensive efforts to improve the nature of blood vessel substitutes, many problems remain, such as an increasing failure rate with decreasing caliber of the blood vessel substitute, a high failure rate when infection supervenes, and biologic failure or degradation by fibrin layering, intimal and subintimal hyperplasia, and aneurysm formation.

A major problem in vascular reconstructive surgery is how effectively to supply blood to organs and tissues whose blood vessels are inadequate either through congenital defects or acquired disorders such as trauma, arteriosclerosis and other diseases. Various techniques and materials have been devised to excise and replace blood vessels, to by pass blood vessels, and to patch, i.e., widen the channel of vessels. Initially arterial homografts (human arteries) were used to restore continuity but limited supply, inadequate sizes, development of aneurysms and arteriosclerosis necessitated the search for a better substitute. A great advance was the development of the partially porous and pliable plastic cloth. Synthetic fibers frequently used as graft material include polyethylene terephthalate (Dacron) and polytetrafluoroethylene (Teflon). Some of the problems experienced with the use of artifically constructed grafts include: (1) infection which may lead to hemorrhage, sepsis and death; (2) the inner lining of the graft is thrombogenic, so that it is predisposed to clotting which may result in total occlusion of the graft and distal embolism of the clot; (3) the rigidity of fabric grafts may result in twisting and kinking especially where a joint is crossed leading to graft occlusion; (4) because of clotting difficulties, smaller caliber artifical grafts are frequently unsuccessful. Many problems posed by artificially manufactured prostheses have led investigators to seek newer and better methods. These include new techniques of "cleaning out" an artery such as by carbodissection, dilating arteries, development of bovine heterografts, creating collagen tubes by inserting a mandrel within the recipient patient for latter use as a graft.

It is known that homografts have been used for vascular grafting with considerable success. Commonly, the saphenous vein has been used in cases where the patient is the donor (an autograft) and where another human is a donor (allograft). These vessels require no treatment before implantation; however; they present problems of unavailability, disparity in size, nonuniform caliber, presence of valves and varicosities, and the need for additional authorization in the case of allografts.

In the present invention, a combined biologic-synthetic vascular graft consisting of umbilical cord vessels surrounded by a synthetic mesh support is provided. The vessels in the human umbilical cord are separated, treated according to the process described herein and used as grafts in vascular reconstructive surgery. The new process described herein relates to the invention of a prosthesis that is unique with respect to origin and morphology. Traditionally discarded after division from the infant at birth, the umbilical cord here finds a new use as the source of valuable grafting materials. It is composed of a vein and two arteries surrounded by a sticky jelly-like substance called Wharton's jelly all encased in the surrounding tissue. The cord varies in length from inches to over three feet in length and is highly flexible. Both the arteries and veins contained therein are suitable for use in vascular surgery. The umbilical cord is fetal tissue in a primitive state giving it the advantage that antigenicity is lower than in adult tissue.

The umbilical cord may be used fresh or it may be preserved for future use. The cord may be freeze-dried, refrigerated, chemically stored or preserved in other known ways. It may require treatment with antibiotics, chemicals, drugs, X-rays and temperature to insure that it is sterile when ready for use. It is antigenic and may require chemical or other known treatment to remove any antigenic substances. Coiled at time of delivery, the cord can be straightened out by mechanical or chemical techniques. Cords obtained from mammals, premature babies, early or terminated pregnancies can also be used to repair smaller vessels.

Until the present discovery, the unique morphology of umbilical cord vessels appeared to render them unsuitable grafting materials. The one vein and two arteries are located together within the protective tissue of the cord; the arteries spiral around the vein in a helical fashion, an occurrence unique in vascular anatomy. This arrangement apparently results in reduced kinking and twisting. Once separated and treated according to the process described herein, the vessels are straight yet remain flexible. They can be shaped to meet the specific needs of the recipient by adjusting the width and length. The grafts prepared can be used as both arterial and venous substitutes; furthermore, they can be used to patch and repair diseased vessels of the body. Finally, it should be noted that the availability of umbilical cords represents a virtually unlimited supply of grafting material for the present invention.

The umbilical cord vessels, especially the arteries, frequently contain valves known as the valves of Hoboken. The presence of these "valves" is one of the factors which has made it unobvious to previous investigators to use these vessels as tubular grafts. In the present process, the valves are treated and eliminated so as to create an unconstricted inner surface within the vessels.

The vessels used as grafts herein are commonly three feet in length thereby eliminating the need for joining several shorter grafts often necessary in vascular surgery involving the arteries or veins of the leg. The diameter of the vessel can also be adjusted by shrinking the vessel during the process and the wall thickness of the vein can also be controlled during the separation step by the amount of tissue removed. The tubes may be slit open longitudinally to obtain a planar graft or patch for repairing vessels of the body. The grafts may be tapered to closely conform in shape to the body's natural vessels.

Tapering also eliminates a major problem associated with autogenous vein grafts as arterial substitutes. Since the saphenous vein contains valves which direct blood flow toward the heart, these grafts must be reversed when used to replace an artery, resulting in a graft which is tapered in the opposite direction to that of the original or host vessel. The graft of the present invention is valveless and readily can be shaped and tapered to the recipient's needs.

The need for additional operations, as in the use of autogenous vein grafts such as the saphenous vein, is obviated by the present discovery. Such operations involve the added risks of prolonged anesthesia, infection, disease and death to the donor.

The advantages of using umbilical cord veins and arteries as vascular grafts may be summarized as follows:
1. availability of grafting material which usually is obtained under sterile conditions (i.e. the operating room at delivery time);
2. ability to be shaped and tapered;
3. absence of valves or branches;
4. flexibility such that the graft can be used across joints;
5. low antigenicity which can be eliminated by the process;
6. use in small vessels without leading to thrombosis;
7. these thin-walled porous vessels permit hardening and tanning agents to penetrate easily during processing; and
8. the graft is entirely preformed, complete when implanted, and may contain an outer mesh support which allows for easy ingrowth of extra fibrocollagenous tissue from outside the graft.

The process described eliminates antigenicity, hardens and strengthens the graft, removes the valves of Hoboken and any varicosities in the vessels, and shaped the vessel to any shape desired. The graft obtained is straight, flexible and can be twisted in any direction. This is a major advantage over autogenous vein grafts which must be implanted in their original shape to avoid minor twists which can lead to closure of the vessel when blood begins to flow through.

Finally, the use of the veins and arteries of the umbilical cord as vascular substitutes has the following advantages during surgical implantation:
1. operating room time (of autografts for example) can be cut down by one to two hours since the need for multiple incisions and the attendant additional procedures are eliminated;
2. a suitable tapered diameter makes it easy to implant the vessel to fit the host vessel to which it is attached;
3. the graft sutures easily and with a minimum bleeding from the needle insertion hole;
4. the lumen of the graft following treatment remains open and does not collapse as does the saphenous vein; and
5. a needle can be inserted into the interstices of the mesh support without harming the graft.

SUMMARY OF THE INVENTION

According to the present invention, the foregoing advantages are obtained by treating the veins and arteries located within the human umbilical cord in the manner described herein. The process produces a prosthesis which obviates many of the disadvantages of previously known grafts.

The present invention concerns a process for producing a tubular prosthesis for vascular reconstructive surgery which comprises the following steps: (a) cleansing the veins and arteries of the umbilical cord to remove blood and residual fluids; (b) removing Wharton's jelly from within the cord; (c) mechanically separating the two arteries and vein from the cord and from one another; (d) eliminating the valves of Hoboken within the vessel; (e) inserting a mandrel to shape the vessel; (f) treating the vessel with a hardening or tanning agent; (g) treating the vessel with an antithrombogenic agent; (h) applying a mesh support externally to the vessels; and (i) implanting the graft so formed.

The prosthesis produced according to this process is intended for use in vascular reconstructive surgery of animals including humans, primates and mammals. It may be used to repair, replace or augment a diseased or defective vein or artery of the body. The thin walled graft may be used as a substitute for the ureter, bile duct and other organs of the body.

Cleansing, rinsing or irrigating solutions which may be employed included water, sterile saline solution, Ringer's lactate solution, hydrogen peroxide, sodium bicarbonate solution, alcohol, and transplantation perfusate solutions.

Antithrombogenic agents which may be used to treat the graft include L-sodium glutamate, L-alanine, L-phenylalanine, L-cysteine, L-lysine.

Wharton's jelly may be removed mechanically or chemically using hyaluronidase to dissolve the hyaluronic acid which comprises the jelly.

The mandrel inserted to shape the vessels and remove the valves of Hoboken may be constructed of an inert material which will not react with the graft vessel or chemicals used in the process. For these purposes glass, silicone, stainless steel or plastic may be used. The mandrel may be straight or curved, solid or hollow, cylindrical or tapered, and smooth or perforated on its surface.

Hardening or tanning agents which may be used to shrink, dilate or otherwise shape the vessel include aldehydes such as glutaraldehyde, dialdehyde starch and formaldehyde, anhydrous alcohol, glyoxal, and chromic oxide.

The mesh support applied to the shaped graft may be made of any non-absorbable synthetic material such as Dacron, Teflon, polyester, polypropylene, Mersilene mesh, plastic and cloth. The mesh is intended to provide support for the graft and should not be absorbed by it or the recipient host tissue readily. The material used must be sterile when implanted.

DESCRIPTION OF PREFERRED EMBODIMENT

EXAMPLE 1

The following example illustrates one manner of processing the umbilical cord blood vessels to obtain vascular substitutes usable in vascular reconstructive surgery. The process involves chemically an structurally modifying the umbilical cord veins and arteries.

The umbilical cord of a newly born infant is taken from the delivery room as soon as possible and washed with 1 percent hydrogen peroxide solution to dissolve blood and fluid remaining within the vessels of the umbilical cord. Blood is removed to prevent staining of the graft tissue. When not contaminated by blood or other fluids, the cord is white in color. The washed cord vessels are gently rinsed with commercially available Ringer's lactate solution.

The cord can be refrigerated and stored to be used weeks later or it can be processed immediately. After washing, the cord is immersed in hyaluronidase solution to dissolve the hyaluronic acid which comprises the sticky subtance known as Wharton's jelly in the umbilical cord. The cord is soaked for 30 minutes in 100 cubic centimeters of a solution containing 150 units of hyaluronidase per cubic centimeter, which is prepared commercially. Once jelly has been removed from the cord, mechanical separation of the vessels is facilitated.

After the cord has been rinsed and soaked in hyaluronidase to remove Wharton's jelly, separation of the vessels from the cord and from one another can take place. A mandrel is inserted through the lumen of the vein of the umbilical cord in order to support the cord during the separation procedure. A smooth, solid, stainless steel mandrel which is tapered from four millimeters at the narrow end to six millimeters at the wide end is used. To separate the arteries from the vein, the mandrel is secured in a vise-like mechanism which also permits rotation of the cord in order to separate the arteries which are spiraling around the vein. The arteries are separated from the cord by passing a spatula or sharp knife between the arteries and the umbilical cord tissue. The separation procedure is facilitated by injecting Ringer's lactate solution between cleavage planes of the arteries and the outer sheath. By gently rotating the mandrel and passing the spatula through the cord longitudinally the outer tissue of the cord is stripped away and the cleavage planes between the vessels are obtained. When most of the tissue has been stripped away, three separate vessels remain, two arteries containing a single distinct layer and a vein in which the wall thickness may be adjusted by removing additional layers of the umbilical cord outer tissue.

When the arteries are separated from the umbilical cord it is necessary to eliminate the valves of Hoboken contained within the lumen of these vessels. The valves are removed by inserting Ringer's lactate solution and glutaraldehyde under pressure using a blunt needle syringe. The force of the fluid passing through the lumen of the artery dilates segments of the vessel, lubricates the inner walls of the vessel and eliminates some of the valves within the artery. The remaining valves are removed by passing a tapered mandrel ranging from 1 to 5 millimeters in diameter through the artery; this has the effect of flattening the inner wall of the vessel uniformly. The arteries so treated no longer contained the valves of Hoboken.

All vessels, the vein and two arteries, can not be shaped and hardened. The mandrels are removed so that the vessels can be rinsed with glutaraldehyde solution for 5 minutes after which the mandrels are reinserted.

The vessels with mandrels in place are then soaked for approximately 60 minutes in a solution of 0.5 percent glutaraldehyde buffered with 1 percent sodium bicarbonate, such that the pH of the solution is in the range 7.0 to 8.5. Glutaraldehyde acts as a hardening or tanning agent and causes the vessel to conform to the size and shape of the mandrel while adding strength to the graft. After 60 minutes, the vessel is removed from the glutaraldehyde solution and rinsed with 1 percent sodium bicarbonate (NaHCO$_3$). However, depending on the degree of hardening desired, the period of soaking in the glutaraldehyde solution may range from 10 minutes to 72 hours. The vessels are treated with 2 percent L-sodium glutamate which reacts with the glutaraldehyde, resulting in an excess of electronegative charges further reducing the possibility of blood clotting. The vessels are again rinsed with sodium bicarbonate and stored in 0.5 percent glutaraldehyde solution.

Following the tanning procedure a polyester mesh support is applied to the graft for added support and strength. Commercially available MERSILENE mesh is used for this purpose. MERSILENE contains wide interstices (0.5–2.0 mm) giving the graft added strength and support while actually imbedding itself into the outer wall of the graft. The mesh support can be either sutured on or rolled on in the form of a preformed sleeve. The graft so prepared can be tested for leaks and strength by attaching it to a pulsating machine and passing solution through it at a pressure of 150 to 300 mm. of mercury. The graft so tested can now be used as a vascular substitute in vascular reconstructive surgery in animals, particularly mammals, primates and humans.

EXAMPLE 2

The following example illustrates the technique of vascular surgical interposition of the umbilical cord vessel derived from the human, into the abdominal aorta of an animal, for example a dog or a baboon.

The animal, in this case a baboon, was prepared under general anesthesia and sterile conditions for making an abdominal incision. The baboon was prepared and shaved and a longitudinal incision was made in the midline of the abdomen. The incision extended from the xythoid to the pubic area and was carried down through the midline and into the peritoneal cavity. Bleeding vessels were clamped and ligated with 3-0 polyglycolic acid sutures. The peritoneal cavity was entered and the viscera and bowel were explored for any other diseases. The animal was found to be normal. The bowel and viscera were walled off with cloth pads and retractors. The peritoneum overlying the aorta was incised and the aorta mobilized by sharp and blunt dissection. Lumbar arteries were individually clamped and ligated with 3-0 silk suture so that the segment of abdominal aorta extending from the infrarenal arteries to the bifurcation of the aorta was mobilized. The entire segment of abdominal aorta was thus made available for transplant of the umbilical cord. During preparation of the abdominal aorta of the baboon, another investigator had taken the umbilical cord of an infant (human) that had been born two hours prior to the surgical intervention of the baboon. The cord had been delivered and taken in its entirety and transported in sterile saline solution, packed in ice. The purpose of freezing the umbilical cord in ice was to prevent any further decomposition of the cord structure. The cord, prior to insertion, was washed and irrigated numerous times with sterile Collins solution and with antibiotics, in this particular instance, 1% cephalosporin solution and 25,000 units of bacitracin per liter of solution. The blood was thoroughly washed out from within the vessels of the cord and the cord was also irrigated with a 1% heparin anticoagulant solution. Following this thorough cleansing of the cord, one end of the umbilical vein within the cord which was to be used as the transplant was clamped with a clamp and through the other end a red rubber catheter, No. 14 French, was introduced and the vein was distended. At this point a suitable segment of umbilical graft, approximately 5 centimeters in length, was selected for excision. This segment of cord was then sterilely handled and placed into the operating field. At this point the animal was heparinized with 2,500 units of aqueous heparin given intravenously. The abdominal aorta was then clamped proximally and distally to the segment to be resected. A segment of approximately 3 centimeters in length was resected from the abdominal aorta and an end-to-end anastomosis was performed between host aorta and donor umbilical vein, using continuous 6-0 prolene. Anastomosis was then completed following flushing of the aorta to rid it of any clot material and debris. Following completion of anastomosis the distal and then the proximal clamps were removed. It was noted that there was no bleeding between the interstices of the sutures, which is unusual, and is felt to be due to the strength and self-sealing gelatinous qualities of the cord structure. Excellent pulses were noted to be present in the graft as well as the distal iliac vessels. The area was lavaged with saline and suctioned. The retroperitoneum was closed with interrupted 3-0 polyglycolic acid sutures and the viscera was replaced. The animal, throughout the procedure thus far, was stable; the respiration and vital signs were normal. The abdominal wall was then closed in layers using continuous 0 silk for the posterior fascia and peritoneum and interrupted 2-0 silk sutures for the anterior fascia. The skin was approximated with continuous 3-0 nylon suture. The anesthesia used in this procedure was nembutal. The blood loss estimated during the procedure was approximately 50 to 75 cubic centimeters. The animal tolerated the procedure well and awoke within 30 minutes. Postoperatively on the following day, the animal was sitting and walking in its cage, and on the third postoperative day was eating its regular diet and was allowed out of its cage to roam around and climb up and down the walls, and appeared to be in excellent health. The legs were warm and pulses were intact in the extremities.

EXAMPLE 3

Implants were performed in female baboons weighing between 12 and 18 kilograms. The anesthesia was induced with one mg/kg of phencyclidine hydrochloride injected intramuscularly and maintained with methoxyflurane, nitrous oxide and oxygen by endotracheal tube or the intravenous pentobarbital sodium. The animals were heparinized systemically with an intravenous bolus injection of 2500 units followed by a continuous drip of 200 units per kilogram per hour for the duration of the vascular procedure. Eight aortoiliac bypasses were performed. The proximal end-to-side anastomosis, performed between the modified human umbilical cord vein graft and the abdominal aorta, was placed below the level of the inferior mesenteric artery. The distal anastomosis was performed end-to-end or end-to-side to either the distal common iliac artery or the proximal external iliac artery. The ipsilateral proximal common iliac artery and internal iliac artery were ligated and divided. In this manner, most of the blood flow to the particular extremity of the baboon was dependent on the vascular graft. The sutures employed in this study consisted of 6-0 monofilament polypropylene. Angiography was performed at the conclusion of the operation and sequentially during the period of observation up to three months. All specimens were studied histologically employing hematoxylin and eosin, Masson's trichrome, Van Giesen and elastic stains.

The modified umbilical cord vein implants with cuffs to the adjacent host artery were removed at intervals of three days to three months. With the exception of one specimen that thrombosed early, presumably due to technical problems, all specimens remained patent and functional for the period of observation. This was confirmed by intraoperative and postoperative angiography. There was no evidence of ectasia or aneurysm formation in any of these specimens. At the time of harvesting the grafts, it was noted that a desmoplastic reaction had occurred about them, particularly after 3 to 4 weeks. Though all of the grafts could be dissected out with relative ease by separation of the outer capsule, it was nonetheless apparent that they were all securely in place prior to their removal from the animals. All cultures of the umbilical cord specimens taken at delivery, implantation and removal from the baboons were negative for routine bacterial growth.

Histologic examination demonstrated a moderately acute inflammatory response in the early specimens consisting of polymorphonuclear leukocytes. This occurred predominantly in the outer capsule around the polyester fiber mesh. There was also a slight inflammatory response about the suture material, but very little reaction in the area of the umbilical vein itself. In later specimens, a chronic inflammatory response consisting of macrophages and occasional foreign body giant cells was again noted around the polyester fiber mesh and to a lesser degree about the suture material. A desmoplastic response was readily identified as an outer capsule. Histologic examination of the inner capsule showed a dense collagen layer adjacent to the mesh. This could be readily demonstrated with standard stains and polarized light and appeared to be primarily a condensation of material preexistent in the cord vessel. Other sites were collagen was present were within the interstices of the mesh and within the inner capsule adjacent to the lumen. A multicellular layer was present at the intimal and subintimal levels. This appeared to be the residual muscular component of the umbilical vein wall, but the possibility exists that fibroblast ingrowth and propagation may also be involved.

EXAMPLE 4

The following example illustrates the implantation of umbilical cord vein grafts into the leg of a human.

An umbilical cord vein graft was prepared generally according to the procedure detailed in Example 1 above. The cord was obtained from an infant delivered 30 days prior to the implantation of the graft. The cord was washed and vessels irrigated with Ringer's lactate solution to remove blood from the umbilical cord. The washed cord was stored in a refrigerator maintained at approximately 4°C for 21 days before processing. At that time, the cord was taken from cold storage, and a tapered mandrel was inserted through the lumen of the vein to straighten the cord and to allow mechanical separation of the vein and arteries from the outer cord tissue. Ringer's lactate solution was injected between the cleavage planes of the arteries which were then separated from the vein.

With the mandrel inserted, the vein was soaked in a solution of 0.5% glutaraldehyde buffered with 1% sodium bicarbonate for one hour. After the tanning and shaping was completed, the vein graft was rinsed with 1% sodium bicarbonate and placed in a bath containing 2% L-sodium glutamate, and antithrombogenic agent. The graft was removed from the bath, rinsed with sodium bicarbonate and fitted with a polyester mesh support. MERSILENE mesh was used for this purpose.

The graft, so prepared was stored in 0.5% glutaraldehyde for one week prior to implantation in the patient.

A male, 72 years of age, with diabetes, developed an ischemic ulcer overlying the lateral malleolus of the left leg. This was associated with an advanced degree of ischemia of the entire foot characterized by coldness, marked rubor on dependancy and significant pallor with elevation. The patient was also unable to walk because of severe claudication. All pulses were absent below the femoral level on the left side. A popliteal pulse was easily palpable on the right side. Femoral angiography showed a severely stenosed superficial femoral artery, with occlusion of the popliteal artery. The posterior tibial and peroneal arteries reconstituted in the lower half of the leg. The anterior tibial artery was well visualized throughout its entire course. A femoral to anterior tibial bypass was performed using the modified umbilical vein graft.

The postoperative course was uneventful, with rapid healing of the ischemic lesion of the ankle. Postoperative angiography confirmed graft patency. The patient is totally asymptomatic and has been followed for three months with easily palpable graft and dorsalis pedis pulses.

EXAMPLE 5

The following example illustrates the results of vascular surgery performed on the leg of a human using the grafts obtained from umbilical cord vessels.

An umbilical cord vein graft was prepared according to the procedure detailed in Example 1 above. The cord was taken from the delivery room and washed with Ringer's lactate solution. To effect mechanical separation of the vessels from the cord and from one another, a tapered mandrel was inserted into the lumen of the umbilical cord vein. When the three vessels were obtained, the vein with the mandrel was treated with 0.5% glutaraldehyde buffered with 1% sodium bicarbonate. The vein graft was soaked in this tanning solution for 30 minutes after which the graft was shaped and hardened. The mandrel was removed and the vessel was rinsed with 1% sodium bicarbonate. A polyester mesh support having 1 mm. interstices was sutured onto the exterior of the graft for support. Commercially available MERSILENE polyester fiber mesh was used for this purpose. The graft so prepared was stored in 0.5% glutaraldehyde and was implanted in the patient the following day in combination with a saphenous vein graft.

A male, 66 years of age, with diabetes developed gangrene and ascending infection of the left hallux, associated with rest pain of the entire foot. All pulses were absent below the femoral level. The infection was controlled with bed rest and antibiotics. Femoral angiography showed severe stenosis and occlusion of the popliteal artery with reconstitution of the posterior tibial artery. A superficial femoral to posterior tibial bypass was performed using a composite graft of modified umbilical vein distally and a 6 inch segment of autogenous saphenous vein proximally. The latter was all that was found to be adequate for use as a graft. Preoperative examination and venography also suggested an inadequate right saphenous vein for use as an arterial graft. The left saphenous vein segment that could be used was insufficient to bridge the entire segment requiring replacement. An umbilical vein graft of approximately 12 inches in length was sutured to the available saphenous vein to form a composite graft.

The composite graft worked effectively with restoration of the posterior tibial pulse. On the sixth postoperative day, acute graft closure occurred and thrombectomy was performed via the saphenous and umbilical components of the graft. Intraoperative angiography, however, failed to show adequate visualization of a pedal arch. Accordingly, the posterior tibial artery was explored at the malleolar level and organized thrombus extracted from the pedal arch with a balloon catheter passed into the foot. Graft patency and function have subsequently been maintained on follow-up for eleven weeks.

EXAMPLE 6

The following example illustrates the results of vascular surgery performed on the leg of a human using the grafts obtained from umbilical cord vessels.

An umbilical cord vein graft was prepared according to the procedure detailed in Example 1. The cord obtained at delivery was washed with 1% hydrogen peroxide and Ringer's lactate solution to remove blood and fluid. The cleansed cord was immersed in a solution containing 150 units per cubic centimeter of hyaluronidase to dissolve Wharton's jelly. After 30 minutes, the cord was removed from the hyaluronidase solution. A tapered mandrel was inserted into the umbilical cord vein to facilitate separation of the three vessels from the outer cord tissue and from one another. The vein was treated to be used in the surgical operation described below. With the mandrel in place, the vein was shaped and hardened for thirty minutes using 0.5% glutaraldehyde buffered with 1% sodium bicarbonate. When tanning was complete, the mandrel was removed and the graft was rinsed with 1% sodium bicarbonate. The graft was treated with an antithrombogenic agent, 2% L-sodium glutamate for 30 minutes and rinsed with sodium bicarbonate. A MERSILENE polyester fiber mesh support was applied to the hardened graft which was then stored in 0.5% glutaraldehyde. The graft was implanted the following day.

A female, 80 years of age, with diabetes had undergone a right femoral prosterior tibial bypass 8 months previously. The graft was constructed as a composite of Dacron and autogenous saphenous vein. The latter was slightly less than 5 millimeters in diameter, but considered adequate. Graft closure occurred 5 months later with recurrence of severe rest and night pain. Mottling of the entire foot was noted, but there were no trophic lesions or gangrene. Graft occlusion with poor runoff by the posterior tibial artery was noted by angiography.

The umbilical vein graft prepared above was placed from the femoral level employing the proximal Dacron cuff to the anterior tibial artery at the midleg level. Compression of the graft was noted as it passed behind the tibia and through an extremely narrow interosseous space. This segment was, therefore, revised by drilling a hole in the tibia and passing the graft through it from the medial aspect of the leg to the anterior tibial artery on the lateral aspect. Postoperatively the foot became warm and all previous complaints referable to ischemia disappeared. The dorsalis pedis pulse could be easily palpated. Graft function and patency were confirmed by postoperative angiography and have been maintained on follow-up for the past four months.

It will be understood that the embodiments described above are merely exemplary and that persons skilled in the art may make many variations and modifications.

Such variations are intended to be within the scope of the invention as defined in the appended claims.

We claim:

1. A process for producing a tubular prostheses for use in vascular reconstructive surgery comprising the steps of washing an umbilical cord to remove blood from within the vessels thereof and distending the vein therein.

2. The process as defined in claim 1, further comprising the step of treating said cord with antibiotics to render said cord sterile.

3. A process for producing a tubular prosthesis for use in vascular reconstructive surgery which comprises the steps of:
   a. removing and separating the internal vein and arteries of the human umbilical cord;
   b. shaping the vein or artery;
   c. treating the vein or artery with a hardening agent; and
   d. applying a mesh support to the external surface of the vein or artery.

4. A process for producing a tubular prosthesis from a human umbilical cord vein or artery for use in vascular reconstructive surgery which comprises the steps of:
   a. removing Wharton's jelly from the human umbilical cord;
   b. mechanically separating the internal veins and arteries from the outer cord tissue and from one another;
   c. eliminating the valves of Hoboken and varicosities within an umbilical cord vein or artery;
   d. inserting a mandrel in the lumen of the vein or artery to shape it;
   e. treating the shaped vein or artery with a tanning or hardening agent; and
   f. reinforcing the formed prosthesis externally with a mesh support.

5. A process for producing a tubular prosthesis for vascular reconstructive surgery from the veins and arteries of the human umbilical cord which comprises the steps of:
   a. cleansing the umbilical cord to remove blood and residual fluid;
   b. removing Wharton's jelly from within the cord;
   c. mechanically separating the two arteries and vein from the umbilical cord and from one another;
   d. eliminating the valves of Hoboken and varicosities within the vein or artery;
   e. inserting a mandrel to shape the vein or artery;
   f. treating the vein or artery with a hardening agent;
   g. treating the vein or artery with an antithrombogenic agent; and
   h. applying a mesh support extermally to the shaped and hardened vein or artery.

6. A process according to claim 5, wherein the cleansing solution used in step (a) is selected from the group consisting of hydrogen peroxide, Ringer's lactate solution, sterile saline solution, water, and transplantation perfusate solutions.

7. A process according to claim 5, wherein Wharton's jelly is removed in step (b) by dissolving it in hyaluronidase solution.

8. A process according to claim 7, wherein the solution used in step (b) has a concentration range of 75 to 1500 units of hyaluronidase per cubic centimeter.

9. A process according to claim 5, wherein Wharton's jelly is removed in step (b) by mechanically separating it from the cord tissue.

10. A process according to claim 5, wherein the arteries are separated from the cord and from each other in step (c) by passing an instrument between the arteries and the outer cord tissue.

11. A process according to claim 5, wherein in step (c) a mandrel is inserted in the umbilical cord vein and said mandrel is fixed in a mechanism to facilitate removal of the outer tissue.

12. A process according to claim 5, wherein the valves are eliminated in step (d) by forcing a fluid through the lumen of the vein or artery.

13. A process according to claim 12, wherein the fluid injected in step (d) is selected from the group consisting of Ringer's lactate solution, glutaraldehyde, sterile saline solution, water, and transplantation perfusate solution.

14. A process according to claim 5, wherein the valves are eliminated in step (e) by passing a mandrel through the lumen of the vein or artery.

15. A process according to claim 5, wherein the mandrel inserted in step (e) is tapered.

16. A process according to claim 15, wherein the mandrel inserted in step (e) is made of inert material.

17. A process according to claim 16, wherein the mandrel inserted in step (e) is solid.

18. A process according to claim 5, wherein the hardening agent used in step (f) is selected from the group consisting of glutaraldehyde and dialdehyde starch, formaldehyde, anhydrous alcohol, glyoxal, and chromic oxide.

19. A process according to claim 18, wherein the hardening agent used in step (f) is buffered with sodium bicarbonate to a pH in the range 7.0 to 8.5.

20. A process according to claim 19, wherein the vessel is treated with the hardening agent from 10 minutes to 72 hours.

21. A process according to claim 5, wherein the antithrombogenic agents used in step (g) are selected from the group consisting of L-alanine, L-sodium glutamate, L-phenylalanine, L-cysteine, and L-lysine.

22. A process according to claim 5, wherein the mesh support used in step (h) is selected from the group consisting or non-absorbable synthetics, polyester fabrics, polypropylene, plastic, cloth, Dacron, Teflon and Mersilene mesh.

23. A process according to claim 5, wherein the mesh support applied in step (h) is sutured onto the graft vessel.

24. A process according to claim 5, wherein the mesh support used in step (h) is in the form of a preformed sleeve.

25. A process according to claim 5, including the step of repairing, replacing or augmenting a diseased or defective vessel of a human or mammal with the tubular prosthesis.

26. A process according to claim 5, including the step of slitting the tubular prosthesis longitudinally to form a thin-walled planar graft.

27. A tubular prosthetic device produced according to claim 5, for repairing, augmenting or replacing a vein or artery of a human, primate, or mammal.

28. A process according to claim 5, wherein the mandrel inserted in step (e) is straight.

29. A process according to claim 5, wherein the mandrel inserted in step (e) is curved.

30. A process according to claim 16, wherein said inert material is stainless steel.

31. A process according to claim 16, wherein said inert material is glass.

32. A process according to claim 16, wherein said inert material is plastic silicone.

33. A process according to claim 16, wherein the mandrel inserted in step (e) is hollow.

34. A process according to claim 16, wherein the mandrel inserted in step (e) is smooth.

35. A process according to claim 16, wherein the mandrel inserted in step (e) is perforated.

36. A tubular prosthesis suitable for repairing, replacing or augmenting a vein or artery of a human, primate or mammal body consisting of a vein or artery of a human umbilical cord that has been separated from the outer umbilical cord tissue, shaped on a mandrel, treated with a hardening agent, treated with an antithrombogenic agent, and fitted with a mesh support.

37. A tubular prosthesis for repairing, augmenting or replacing a vein or artery of a mammal comprising an umbilical cord essentially free of blood and having therein a vein in distended condition.

38. A tubular prosthesis suitable for repairing or augmenting a vein or artery of a human, primate or mammal body, comprising a human umbilical cord vessel having a shape other than that in which it occurs in nature and having a hardness greater and a thrombogenicity lower than it has in its natural state as a prosthesis, and a mesh support fitted to said vessel, said vessel being free of outer umbilical cord tissue.

39. The tubular prosthesis as defined in claim 38, wherein said vessel is also freed of Hoboken valves and varicosities.

* * * * *